United States Patent [19]
Gorenbein et al.

[11] Patent Number: 5,955,102
[45] Date of Patent: Sep. 21, 1999

[54] SOFTGEL CAPSULE CONTAINING DHA AND ANTIOXIDANTS

[75] Inventors: David Gorenbein, Costa Mesa; Nagui Ibrahim, Fountain Valley, both of Calif.

[73] Assignee: Amway Corporation, Mich.

[21] Appl. No.: 09/148,567

[22] Filed: Sep. 4, 1998

[51] Int. Cl.⁶ .............................. A61K 9/48; A61K 65/00
[52] U.S. Cl. ..................... 424/451; 424/195.1; 424/441; 424/455; 424/456; 426/250; 426/311; 426/544; 426/573; 426/648; 426/655; 514/558
[58] Field of Search ................................. 424/195.1, 441, 424/456, 4.55, 451; 426/544, 573, 250, 31.1, 648, 655; 514/558

[56] References Cited

U.S. PATENT DOCUMENTS 5,484,611 1/1996 Noble et al. .............................. 424/451
5,804,168 9/1998 Murad et al. .............................. 424/59
5,827,652 10/1998 Garnett et al. .......................... 424/451

OTHER PUBLICATIONS

ACS Computer Caplus Abstract Verakunpiriya et al Jour. Fish Sci "Effect of brookstock diets on the chemical components of milt and eggs produced by yellowtail" Jour. Fish. Sci. (1996) 62(4) 61–619, 1996.

*Primary Examiner*—Herbert J. Lilling
*Attorney, Agent, or Firm*—Brinks Hofer Gilson & Lione

[57] ABSTRACT

This invention provides a nutritional supplement containing docosahexaenoic acid (DHA), antioxidants and anthocyanosides. The supplement is useful for improving night vision acuity, field of vision and adaptation to light.

16 Claims, No Drawings

SOFTGEL CAPSULE CONTAINING DHA AND ANTIOXIDANTS

BACKGROUND OF THE INVENTION

1. Field of the invention

This invention provides a nutritional supplement containing docosahexaenoic acid (DHA), lutein and anthocyanosides. The supplement is useful for improving night vision acuity, field of vision and adaptation to light.

2. Discussion of the Background:

Docosahexaenoic acid (DHA) and eicosapentaenoic acid (EPA) are omega-3 ($\omega$3) polyunsaturated fatty acids (PUFA) found naturally in marine oils. Both DHA and EPA have beneficial pharmacological effects on the human cardiovascular system, the auto-immune system and the development and maintenance of the brain and retina functions. DHA is present in large amounts in the outer segments (phospholipids) or photoreceptor cells of the retina (Murphy MG, *J. Nutr. Biochem.* 1990, 1: 69–70). Although the role of DHA in retinal function has been questioned (See Leaf et al, *Early Human Dev.* 1996, 45:35–53; Weisinger et al., *Lipids* 1996, 31:65–70), it is widely believed to be beneficial (See Noble et al., U.S. Pat. 5,484,611). DHA is critical for normal retinal development, and continues to accumulate in the retina even after birth, suggesting that it is a vital nutrient Conner WE et al., *World Review in Nutrition and Dietetics* 1991, 66:118–32).

Antioxidants are believed to extend normal vision by preventing cataract formation (See Taylor, *J. Am. Coll Nutr.* 1993, 12:138–46) and other visual disorders (Richer, *J. Am. Optom. Assoc.* 1996, 67:30–49). Lutein and zeaxanthin are antioxidants, belonging to a class of lipid-soluble yellow-to-red pigments known as carotenoids. In humans, lutein and zeaxanthin are major constituents of the macula lutea region of the retina, which is responsible for sharp, detailed viewing (Bone RA et al., *Invest. Ophthalmol. Vis. Sci.* 1993, 34:3033–40).

Anthocyanosides are a group of red to blue plant pigments, which exist as condensed products (glycosides) of anthocyanins or anthocyanidins combined usually with sugar, such as glucose, arabinose or galactose. Bilberry contains a variety of anthocyanosides including cyanidine, malvidine, delphynidine, petunidine and peonidiene. Anthocyanosides are similar in structure and function to bioflavonoids. In particular, anthocyanosides enhance the regeneration of rhodopsin or visual purple, an eye protein necessary for vision in dim light or at night. Anthocyanosides may also improve vision by enhancing the activity of metabolic enzymes in the retina. (See De Smet, P. (1983) "Vaccinium myrtillus," In *Adverse Effects of Herbal Drugs*, De Smet et al eds., pp. 307–314, Berlin: Springer-Verlag; Cunio, L. *Austrian J. Medicinal Herbalism* 1993, 5(4): 81–85; Mowrey, E. (1990) "Bilberry: For veins, eyes and nerves." In *Guaranteed Potency Herbs: Next Generation Herbal medicine*, pp. 14–24, New Canaan: Keats Publishing Inc.).

Despite the recognition of the beneficial properties of DHA, antioxidants such as lutein and anthocyanosides, the American diet contains few foods which supply these nutrients. Thus, a nutritional supplement comprising these is desirable. Such a nutritional supplement is particularly useful for preventing visual disorders and for improving vision.

SUMMARY OF THE INVENTION

The present invention provides a nutritional supplement useful for preventing visual disorders and for improving vision. The nutritional supplement comprises DHA, antioxidants including at least lutein, and anthocyanosides.

The present invention also provides a method of correcting, improving, preventing, or delaying various visual disorders such as myopia, hemeralopia, eye strain, night vision, retinal and macular degeneration.

DETAILED DESCRIPTION OF THE INVENTION

In accordance with the present invention, a nutritional supplement is provided which includes at least DHA, lutein and anthocyanosides as active ingredients.

As used herein, an "anthocyanoside" is a flavonoid plant pigment which accounts for most of the red, pink, and blue colors in plants, fruits, and flowers.

A "carotenoid" is a class of pigments occurring in the tissues of higher plants, algae, bacteria and fungi. They are usually yellow to deep red, crystaline solids, soluble in fats and oils, insoluble in water, high melting, stable to alkali, unstable to acids and oxidizing agents, their color is easily destroyed by hydrogenation or by oxidation, and some are optically active.

A "flavonoid" is a group of aromatic, oxygen-containing, heterocyclic pigments widely distributed among higher plants. They constitute most of the yellow, red, and blue colors in flowers and fruits, excluding the carotenoids. The flavonoids include the following subgroups: (1) catechins, (2) leucoanthocyanidins and flavanones, (3) flavanins, flavones, and anthocyanins, and (4) flavonols.

The nutritional supplement of the present invention is preferably provided as a capsule and includes a liquid or dry inner filling and an outer shell. In the preferred embodiment, the inner filling is a liquid mixture which is contained within a gelatin capsule, such as a "softgel" type capsule.

The inner filling includes at least DHA, lutein and at least one anthocyanoside. "DHA" refers to the free acid form of docosahexaenoic acid, not the phospholipid form or the ester form. One naturally occurring source of DHA is fish oil. Fatty fish such as salmon, mackerel, sardines, ocean trout and herring contain the highest amounts of DHA (about 600–800 mg/3 oz). Other sources of DHA include fin fish such as whiting and flounder (about 200–400 mg/ 3 oz), plants such as seaweeds, and many microorganisms.

The nutritional supplement of the present invention preferably contains about 25 to 900, preferably 25 to 140, mg/day of DHA. Alternatively, the nutritional supplement contains 10 to 15% by weight of DHA.

EPA, another $\omega$3 PUFA, is commonly found in sources of DHA. When EPA is present, the ratio of DHA:EPA in the nutritional supplement is greater than 1.1:1, preferably greater than 2:1, and more preferably greater than 4:1. Tuna oil is the preferred source of DHA as it contains about 25% DHA and about 6% EPA.

Lutein and zeaxanthin are both carotenoids and structural isomers of one another. They can be extracted in crystalline form from marigolds. Dietary sources of lutein and zeaxanthin include mustard greens, spinach, kale, broccoli, leaf lettuce, green peas, brussel sprouts, corn, some squash and green beans.

The nutritional supplement of the present invention preferably contains about 1 to 6 mg/day of lutein. Alternatively, the nutritional supplement contains 0.1 to 0.5% by weight of lutein.

The nutritional supplement of the present invention preferably contains about 0 to 0. 15 mg/day of zeaxanthin.

Alternatively, the nutritional supplement contains 0 to 0.05% by weight of zeaxanthin.

In addition to lutein and zeaxanthin, other antioxidants may also be present in the nutritional supplement of this invention. These may include vitamins such as vitamin A, vitamin C, and vitamin E ( -tocopherol) or lemon bioflavonoids. The nutritional supplement may contain 0 to 10% by weight of one or more antioxidants.

Any source of anthocyanosides can be used in accordance with the present invention. Bilberry extract is preferred. "Bilberry" refers to berries of *Vaccinium myrtillus*, a small, perennial scrub that is native to northern Europe and Asia. Other names include blueberry, whortleberry, black whortles, shinberry, trackleberry, hurts, bleaberry, hurtleberry and airelle.

The nutritional supplement of the present invention preferably contains about 3 to 200, preferably about 30 to 200, mg/day of an anthocyanoside such as bilberry extract. Alternatively, the nutritional supplement contains 5 to 10% by weight of an anthocyanoside such as bilberry extract.

The components of the inner filling are preferably solubilized in a liquid to form a liquid mixture (i.e., not an emulsion). Suitable liquids include vegetable oils such as soybean oil. The inner filling can other components, including fillers, components useful for adjusting the isotonic properties of the filling (such as glycerol), and components useful for adjusting the stability of the inner filling such as amino acids and carbohydrates (such as fructose, glucose, dextrose, etc.).

When the inner filling of the nutritional supplement of the present invention is a liquid, the outer shell is preferably composed of gelatin as well as other optional components such as glycerol and coloring agents (such as caramel). Such a nutritional supplement can be obtained by filling the outer shell with the premixed inner filling.

In one particularly preferred embodiment, the nutritional supplement is a softgel capsule comprising (i) about 70% by weight, based on the total weight of the capsule, of an inner filling comprising: about 8% by weight of bilberry extract, about 0.3% by weight of lutein, about 0.01% by weight of zeaxanthin, about 12% by weight of DHA, about 3% by weight of EPA, about 6% by weight of vitamin C, and about 6% by weight of lemon bioflavonoids; and (ii) about 30% by weight, based on the total weight of the capsule, of an outer shell comprising about 20% by weight, based on the total weight of the capsule, of gelatin.

Having generally described this invention, a further understanding can be obtained by reference to the following example which is provided herein for purposes of illustration only and is not intended to be limiting.

EXAMPLE
Formulation of a Softgel Capsule

The following softgel capsule is one embodiment of the present invention. To provide a benefit to vision, two such softgel capsules would be ingested per day.

| Ingredient | genus/species | ingredient breakdown | mg/ softgel |
| --- | --- | --- | --- |
| Inner filling | | | |
| bilberry extract | *Vaccinium myrtillus* | 90% Bilberry extract 7% Fructose 3% Dextrsoe | 40 |
| marigold extract | *Tagetes Erecta* | 20% Lutein 0.86% Zeaxanthin 79.14% Corn oil | 7.5 |
| tuna oil | | 25% DHA 6% EPA 0.2% Spearmint | 200 |
| acerola concentrate | *Malpighia emarginata* | | 25 |
| lemon biflavonoids | *Citrus limon* | | 25 |
| soy lecithin | | | 12 |
| vegetable oil (soya) | | | 61.52 |
| -tocopherol | | 67% -tocopherol 33% soy oil | 1 |
| yellow beeswax | | | 41 |
| Outer shell | | | |
| gelatin | | | 134.98 |
| glycerin | | | 59.72 |
| caramel color | | | 4.98 |

Having now fully described the invention, it will be apparent to one of ordinary skill in the art that many changes and modifications can be made thereto without departing from the spirit or scope of the invention as set forth herein.

We claim:

1. A nutritional supplement comprising as active ingredients docosahexaenoic acid (DHA), lutein, and at least one anthocyanoside.

2. The nutritional supplement of claim 1, comprising as active ingredients:
   about 25 to 900 mg/day of DHA,
   about 1 to 6 mg/day of lutein, and
   about 3 to 200 mg/day of at least one anthocyanoside.

3. The nutritional supplement of claim 1, further comprising zeaxanthin.

4. The nutritional supplement of claim 1, wherein said anthocyanoside is bilberry extract.

5. The nutritional supplement of claim 2, wherein said anthocyanoside is bilberry extract.

6. The nutritional supplement of claim 5, further comprising about 1 to 500 mg vitamin C.

7. A method of improving the vision of a patient in need thereof, comprising consuming a nutritional supplement comprising as active ingredients:
   about 25 to 900 mg/day of docosahexaenoic acid (DHA),
   about 1 to 6 mg of lutein, and
   about 3 to 200 mg of at least one anthocyanoside.

8. A nutritional supplement, comprising as active ingredients:
   about 25 to 140 mg docosahexaenoic acid (DHA),
   about 1 to 6 mg lutein, and
   about 30 to 200 mg bilberry extract.

9. The nutritional supplement of claim 8, further comprising about 0.1 to 0.25 mg of zeaxanthin.

10. The nutritional supplement of claim 8, further comprising about 20 to 30 mg of EPA, wherein the ratio DHA:EPA is greater than 1.1:1.

11. The nutritional supplement of claim 10, wherein the ratio DHA:EPA is greater than 2:1.

12. The nutritional supplement of claim 11, wherein the ratio DHA:EPA is greater than 4:1.

13. The nutritional supplement of claim 8, further comprising about 1 to 40 mg of vitamin C.

14. The nutritional supplement of claim 8, further comprising about 1 to 80 mg of lemon bioflavonoids.

15. A softgel capsule comprising:
(i) about 50 to 90% by weight, based on the total weight of the capsule, of an inner filling comprising:
   about 5 to 10% by weight, based on the total weight of the capsule, of bilberry extract,
   about 0.1 to 0.5% by weight, based on the total weight of the capsule, of lutein,
   about 0 to 0.05% by weight, based on the total weight of the capsule, of zeaxanthin,
   about 10 to 15% by weight, based on the total weight of the capsule, of DHA,
   about 0 to 10% by weight, based on the total weight of the capsule, of one or more antioxidants selected from the group consisting of vitamin C, vitamin E, vitamin A, and bioflavonoids; and
(ii) about 10 to 50% by weight, based on the total weight of the capsule, of an outer shell comprising about 20% by weight, based on the total weight of the capsule, of gelatin.

16. The softgel capsule of claim 15, comprising:
(i) about 70% by weight, based on the total weight of the capsule, of an inner filling comprising:
   about 8% by weight, based on the total weight of the capsule, of bilberry extract,
   about 0.3% by weight, based on the total weight of the capsule, of lutein,
   about 0.01% by weight, based on the total weight of the capsule, of zeaxanthin,
   about 12% by weight, based on the total weight of the capsule, of DHA,
   about 3% by weight, based on the total weight of the capsule, of EPA,
   about 6% by weight, based on the total weight of the capsule, of vitamin C, and
   about 6% by weight, based on the total weight of the capsule, of lemon bioflavonoids; and
(ii) about 30% by weight, based on the total weight of the capsule, of an outer shell comprising about 20% by weight, based on the total weight of the capsule, of gelatin.

* * * * *